United States Patent [19]
Lambert et al.

[11] Patent Number: 4,882,316
[45] Date of Patent: Nov. 21, 1989

[54] PYRIMIDINE DERIVATIVES

[75] Inventors: Robert W. Lambert, Welwyn; Joseph A. Martin, Harpenden; Gareth J. Thomas, Welwyn, all of England

[73] Assignee: Hoffmann-La Roche Inc., Nutley, N.J.

[21] Appl. No.: 79,741

[22] Filed: Jul. 30, 1987

[30] Foreign Application Priority Data

Aug. 8, 1986 [GB] United Kingdom ............... 8619424
May 7, 1987 [GB] United Kingdom ............... 8710777

[51] Int. Cl.⁴ .................... A61K 31/70; C07H 19/07; C07D 405/04; C07D 403/00
[52] U.S. Cl. .................................. 514/49; 514/50; 536/23
[58] Field of Search ................ 536/23; 514/49, 50

[56] References Cited

U.S. PATENT DOCUMENTS 4,000,260 12/1976 Prusoff et al. .................. 514/50

FOREIGN PATENT DOCUMENTS 2548190 1/1985 France .

OTHER PUBLICATIONS

Elliott et al. "Jour. Medicinal Chem." 1981 vol. 24 #3; pgs. 350-352.
Hampton et al., J. of Med. Chem., vol. 22, No. 12, pp. 1524-1528 (1979).
Setsuro et al., The Chemical Abstracts, 86: 16907n (1977).
Montgomery et al., The Chemical Abstracts 100: 156925z (1984).
Markham et al., Antiviral Research No. 2, pp. 319-330 (1982).

*Primary Examiner*—Herbert J. Lilling
*Attorney, Agent, or Firm*—Jon S. Saxe; Bernard S. Leon; Matthew Boxer

[57] ABSTRACT

Compounds of the formula

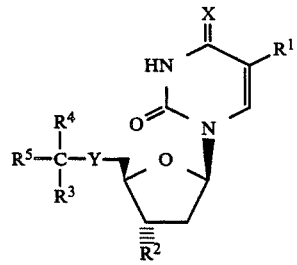

wherein $R^1$ is halogen, $C_{1-4}$-alkyl or halo-($C_{1-4}$-alkyl), $R^2$ is hydrogen, hydroxy or acyloxy, $R^3$ and $R^4$ each are hydrogen or $C_{1-4}$-alkyl, $R^5$ is aryl or aryloxy, X is O or NH and Y is $-CO-CH_2-$, $-CH(OH)-CH_2-$, $-CH_2-CH_2-$, $-S-$, $-SO-$ or $-SO_2-$, and tautomers thereof are described. Compounds of formula I and their tautomers possess antiviral activity and can be used in the form of medicaments for the control and prevention of viral infections.

15 Claims, No Drawings

PYRIMIDINE DERIVATIVES

BRIEF SUMMARY OF THE INVENTION

The invention is concerned with pyrimidine derivatives, a process for their manufacture and medicaments containing said derivatives.

These pyrimidine derivatives are compounds of the formula

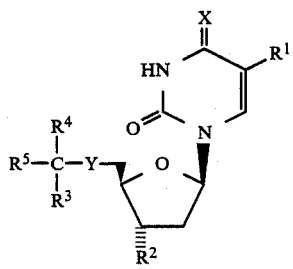

I wherein $R^1$ is halogen, $C_{1-4}$-alkyl or halo-($C_{1-4}$-alkyl), $R^2$ is hydrogen, hydroxy or acyloxy, $R^3$ and $R^4$ each are hydrogen or $C_{1-4}$-alkyl, $R^5$ is aryl or aryloxy, X is O or NH and Y is —CO—CH$_2$—, —CH(OH)—CH$_2$—, —CH$_2$—CH$_2$—, —S—, —SO— or —SO$_2$—, and tautomers thereof. The compounds of formula I and their tautomers are useful as antiviral agents.

DETAILED DESCRIPTION OF THE INVENTION

As used herein, "$C_{1-4}$-alkyl" means a straight- or branched-chain alkyl group, such as methyl, ethyl, propyl, isopropyl, butyl or t-butyl etc. "Halo-($C_{1-4}$-alkyl)" means an alkyl group as defined earlier carrying one or more halogen atoms; e.g. trifluoromethyl or 2-chloroethyl. The acyloxy group can be derived from an aliphatic, cycloaliphatic, araliphatic or aromatic carboxylic acid, examples of such acids being formic acid, acetic acid, propionic acid, butyric acid, cyclopentylpropionic acid, phenylacetic acid and benzoic acid. Preferred acyloxy groups are $C_{1-4}$-alkanoyloxy group. "Aryl" means unsubstituted phenyl group or a phenyl carrying one or more substituents selected from halogen, hydroxy, $C_{1-4}$-alkyl, $C_{1-4}$-alkoxy, trifluoromethyl, nitro and phenyl. Examples of such substituted-phenyl groups are 2-chlorophenyl, 2,4- or 2,6-dichlorophenyl, 2-methylphenyl and 2,6-dimethylphenyl. "Aryloxy" means an aryl group as defined above which is bonded via an oxygen atom. Examples of aryloxy groups are phenoxy, 2-chlorophenoxy and 2,4-dichlorophenoxy. "Halogen" means fluorine, chlorine, bromine or iodine. When Y is —CO—CH$_2$— or —CH(OH)—CH$_2$—, the compounds of formula I have the formulae

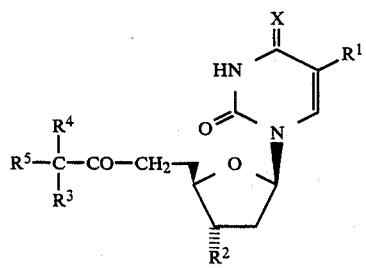

and

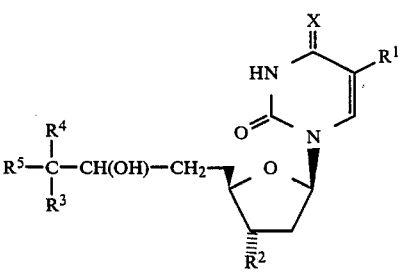

respectively.

As used herein the symbol (E)

—CH=CH— in a structural formula denotes

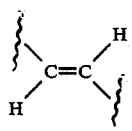

Similarly, the term ("E") as it appears in the chemical nomenclature denotes the same stereochemical conformation as appears just above.

The invention relates to compounds of the formula

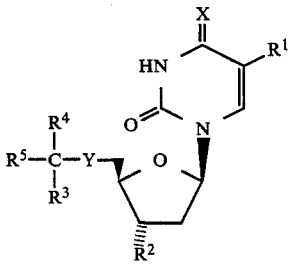

I wherein $R^1$ is halogen, $C_{1-4}$-alkyl or halo-($C_{1-4}$-alkyl), $R^2$ is hydrogen, hydroxy or acyloxy, $R^3$ and $R^4$ each are hydrogen or $C_{1-4}$-alkyl, $R^5$ is aryl or aryloxy, X is O or NH and Y is —CO—CH$_2$—, —CH(OH)—CH$_2$—, —CH$_2$—CH$_2$, —S—, —SO— or —SO$_2$—, and tautomers thereof. The compounds of formula I and their tautomers are useful as antiviral agents.

The compounds of formula I and their tautomers in which Y is —CH(OH)—CH$_2$— or in which $R^3$ and $R^4$ are different i.e. when $R^3$ is a hydrogen atom and $R^4$ is a $C_{1-4}$-alkyl group or when $R^3$ and $R^4$ each are different $C_{1-4}$-alkyl groups, contain an asymmetric carbon atom and can accordingly exist as diastereoisomers. The invention relates not only to individual diastereoisomers, but also to mixtures thereof.

In formula I above $R^1$ preferably is $C_{1-4}$-alkyl especially ethyl. $R^2$ preferably is hydroxy or $C_{1-4}$-alkanoyloxy, especially hydroxy or acetoxy. $R^3$ and $R^4$ each preferably are hydrogen. $R^5$ preferably is dihalophenyl, especially 2,6-dichlorophenyl. X preferably is O. Y preferably is —CO—CH$_2$—, —CH(OH- )—CH₂—, —CH₂—CH₂— or —SO₂—, especially —CO—CH₂— or —CH(OH)—CH₂—.

Especially preferred compounds of the invention are those in which R¹ is ethyl, R² is hydroxy or acetoxy, R³ and R⁴ each are hydrogen, R⁵ is 2,6-dichlorophenyl, X is O and Y is —CO—CH₂— or —CH(OH)—CH₂—.

Particularly preferred compounds of formula I are:
3'-O-Acetyl-5'-[3-(2,6-dichlorophenyl)-2-oxopropyl]-2',5'-dideoxy-5-ethyluridine,
5'-[3-(2,6-dichlorophenyl)-2-oxopropyl]-2',5'-dideoxy-5-ethyluridine and
5'-[3-(2,6-dichlorophenyl)-2(RS)-hydroxypropyl]-2',5'-dideoxy-5-ethyluridine.

Other preferred compounds of formula I are:
3'-O-Acetyl-2',5'-dideoxy-5-ethyl-5'-[3-(2,6-dimethylphenyl)-2-oxopropyl]uridine,
3'-O-acetyl-2',5'-dideoxy-5-ethyl-5'-[3-(2-methylphenyl)-2-oxopropyl]uridine,
3'-O-acetyl-5'-[3-(2-chlorophenyl)-2-oxopropyl]-2',5'-dideoxy-5-ethyluridine,
3'-O-acetyl-2',5'-dideoxy-5-ethyl-5'-(2-oxo-3-phenylpropyl)uridine,
3'-O-acetyl-2',5'-dideoxy-5-ethyl-5'-[2-oxo-3(RS)-phenylbutyl]uridine,
2',5'-dideoxy-5-ethyl-5'-(2-oxo-3-phenylpropyl)uridine,
2',5'-dideoxy-5-ethyl-5'-[3-(2-methylphenyl)-2-oxopropyl]uridine,
2',5'-dideoxy-5-ethyl-5'-[3-(2,6-dimethylphenyl)-2-oxopropyl]uridine,
5'-[3-(2-chlorophenyl)-2-oxopropyl]-2',5'-dideoxy-5-ethyluridine,
2',5'-dideoxy-5-ethyl-5'-[2-oxo-3(RS)-phenylbutyl]uridine,
2',5'-dideoxy-5-ethyl-5'-[2(RS)-hydroxy-3-phenylpropyl]uridine,
2',5'-dideoxy-5-ethyl-5'-[2(RS)-hydroxy-3-(2-methylphenyl)propyl]uridine,
5'-[3-(2-chlorophenyl)-2(RS)-hydroxypropyl]-2',5'-dideoxy-5-ethyluridine,
2',5'-dideoxy-5-ethyl-5'-[2(RS)-hydroxy-3-(2,6-dimethylphenyl)propyl]uridine,
2',5'-dideoxy-5-ethyl-5'-(3-phenylpropyl)uridine and
5'-benzylsulphonyl-2',5'-dideoxy-5-ethyluridine.

Other interesting compounds of formula I are:
2',5'-Dideoxy-5'-[3-(2,6-dimethylphenyl)-2-oxopropyl]uridine,
3'-O-acetyl-5'-[3(RS)-(2,4-dichlorophenoxy)-2-oxobutyl]2',5'-dideoxy-5-ethyluridine,
5'-[3(RS)-(2,4-dichlorophenoxy)-2-oxobutyl]-2',5'-dideoxy-5-ethyluridine,
5'-[3(RS)-(2,4-dichlorophenoxy)-2(RS)-hydroxybutyl]2',5'-dideoxy-5-ethyluridine,
5'-benzylthio-2',5'-dideoxy-5-ethyluridine,
5'-(2-chlorobenzylthio)-2',5'-dideoxy-5-ethyluridine,
5'-(2,4-dichlorobenzylthio)-2',5'-dideoxy-5-ethyluridine,
5'-(2,6-dichlorobenzylthio)-2',5'-dideoxy-5-ethyluridine,
5'-(2-chlorobenzylsulphonyl)-2',5'-dideoxy-5-ethyluridine,
5'-(2,4-dichlorobenzylsulphonyl)-2',5'-dideoxy-5-ethyluridine and
5'-(2,6-dichlorobenzylsulphonyl)-2',5'-dideoxy-5-ethyluridine According to the process of the invention, the compounds of formula I above and their tautomers are manufactured by (a) for the manufacture of a compound of formula I or a tautomer thereof in which R² is hydrogen or acyloxy and Y is —CO—CH₂—, catalytically hydrogenating a compound of the formula

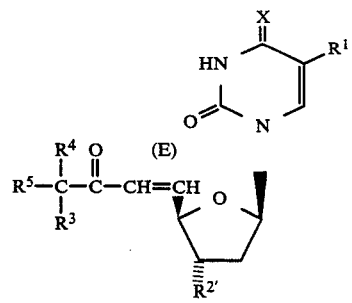

wherein R¹, R³, R⁴, R⁵ and X are as described above and R²' is hydrogen or acyloxy,
or a tautomer thereof, or (b) for the manufacture of a compound of formula I or a tautomer thereof in which R² is hydrogen or acyloxy and Y is —CH(OH)—CH₂—, reducing a compound of formula I or a tautomer thereof in which R² is hydrogen or acyloxy and Y is —CO—CH₂—, with a complex metal hydride, or (c) for the manufacture of a compound of formula I or a tautomer thereof in which R² is hydrogen or acyloxy and Y is —CH₂—CH₂—, replacing the hydroxy group in a compound of formula I or a tautomer thereof in which R² is hydrogen or acyloxy and Y is —CH(OH)—CH₂— by hydrogen, or (d) for the manufacture of a compound of formula I or a tautomer thereof in which Y is —S—, reacting a compound of the formula

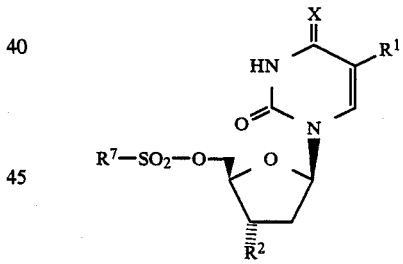

wherein R¹, R² and X are as described above and R⁷ is C₁₋₄-alkyl or aryl,
or a tautomer thereof with an alkali metal derivative of a compound of the formula

HSC(R³,R⁴,R⁵)  IV wherein R³, R⁴ and R⁵ are as described above,
at an elevated temperature, or (e) for the manufacture of a compound of formula I or a tautomer thereof in which Y is —SO— or —SO₂—, oxidizing a compound of formula I or a tautomer thereof in which Y is —S—, or (f) for the manufacture of a compound of formula I or a tautomer thereof in which R² is hydroxy, deacylating a compound of formula I or a tautomer thereof in which R² is acyloxy.

The catalytic hydrogenation in accordance with embodiment (a) of the process can be carried out in a manner known per se, e.g. in an inert organic solvent, such as an alkanol, e.g. methanol or ethanol, using a noble-metal catalyst, such as a palladium or platinum catalyst, which may be supported on an inert carrier material. Palladium-on-carbon (Pd/C) is the preferred catalyst. Conveniently, the catalytic hydrogenation is carried out at about room temperature and under atmospheric pressure.

The reduction in accordance with embodiment (b) of the process can be carried out in a manner known per se, e.g. by treatment with sodium borohydride or potassium borohydride or, when $R^2$ is hydrogen, also with lithium borohydride or an alkali metal aluminium hydride, such as lithium aluminium hydride. This treatment is conveniently carried out in an inert organic solvent and at room temperature to the reflux temperature of the mixture, preferably at about room temperature. When the reduction is carried out using an alkali metal borohydride, suitable solvents are alkanols, e.g. methanol or ethanol, aliphalic ethers, e.g. diethyl ether or dimethoxyethane, and cyclic ethers, e.g. tetrahydrofuran and dioxan. Suitable solvents which can be used when the reduction is carried out using an alkali metal aluminium hydride are aliphatic and cyclic ethers such as those mentioned earlier.

The replacement of hydroxy by hydrogen in accordance with embodiment (c) of the process can also be carried out in a manner known per se. For example, the compound of formula I or a tautomer thereof can firstly be converted into the corresponding sulphonic acid ester, such as the mesylate, by treatment with a sulphonic acid halide, such as methanesulphonyl chloride, conveniently in the presence of an acid binding agent, especially a tertiary amine, such as pyridine, and at a low temperature, e.g. about 0° C. The obtained sulphonic acid ester can then be converted into the corresponding iodide, e.g. by treatment with an alkali metal iodide, such as sodium iodide, in acetone at an elevated temperature, preferably at the reflux temperature of the mixture. The resulting iodide can then be converted into the desired compound of formula I or a tautomer thereof in which Y is —CH$_2$—CH$_2$— by catalytic hydrogenation in a known manner, e.g. using a palladium on barium sulphate catalyst.

In the reaction of a compound of formula III or a tautomer thereof with an alkali metal derivative, preferably the sodium derivative, of a compound of formula IV in accordance with embodiment (d) of the process the $R^7$—SO$_2$— group is displaced by the —SC($R^3$,$R^4$,$R^5$) group. The reaction is conveniently carried out in the presence of an inert organic solvent such, as dimethylformamide, and at about 100° C. The alkali metal derivative is expediently formed in situ from the compound of formula IV and an alkali metal hydride, such as sodium hydride.

The oxidation in accordance with embodiment (e) of the process can also be carried out in a manner known per se. For example, a compound of formula III or a tautomer thereof is treated with an organic peracid, such as peracetic, perbenzoic, m-chloroperbenzoic or perphthalic acid, expediently in a suitable solvent, such as a halogenated hydrocarbon, e.g. chloroform, or an alkanoic acid, e.g. acetic acid and at a temperature between about 0° C. and room temperature. When peracetic acid is used for the oxidation, this can conveniently be prepared in situ from glacial acetic acid and hydrogen peroxide. When 1 equivalent of an organic peracid is used there is obtained a compound of formula I or a tautomer thereof in which Y is —SO—, whereas the use of 2 equivalents of organic peracid leads to a compound of formula I or a tautomer thereof in which Y is —SO$_2$—.

The deacylation in accordance with embodiment (f) of the process can be carried out in a manner known per se, e.g. by treatment with an alkali metal C$_{1-4}$-alkoxide, such as sodium methoxide, in a C$_{1-4}$-alkanol, such as methanol. Conveniently, this treatment is carried out at about room temperature, although it may be carried out at an elevated temperature is desired.

The compounds of formula II and tautomers thereof which are used as starting materials in embodiment (a) of the present process are novel and also form an object of the present invention. They can be prepared, for example, by firstly reacting a compound of the formula

$$ClCH_2COC(R^3,R^4,R^5) \quad\quad V$$

wherein $R^3$, $R^4$ and $R^5$ are as described above, with a triarylphosphine, preferably triphenylphosphine, conveniently in an inert organic solvent, such as a halogenated hydrocarbon, e.g. chloroform, and at an elevated temperature, suitably at the reflux temperature of the reaction mixture, to give a phosphonium chloride of the formula

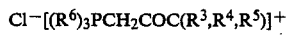

$$Cl^-[(R^6)_3PCH_2COC(R^3,R^4,R^5)]^+ \quad\quad VI$$

wherein $R^3$, $R^4$ and $R^5$ are as described above and $R^6$ is aryl.

The phosphonium chloride of formula VI is then treated with a strong inorganic base, such as an alkali metal hydride, e.g. sodium hydride, or an alkali metal hydroxide, e.g. sodium hydroxide, and the resulting phosphorane of the formula

$$(R^6)_3P=CHCOC(R^3,R^4,R^5) \quad\quad VII$$

wherein $R^3$, $R^4$, $R^5$ and $R^6$ are as described above, is finally reacted with a compound of the formula

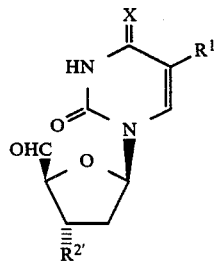

wherein $R^1$, $R^{2'}$ and X are as described above, or a tautomer thereof under the conditions of a Wittig reaction to give a compound of formula II.

The compounds of formula V, which are required for the preparation of the compounds of formula II and their tautomers, are known compounds or analogues of known compounds which can be prepared in a similar manner to the known compounds. The compounds of formula III and their tautomers, which are used as starting materials in embodiment (d) of the present process are known compounds or analogues of known compounds which can be prepared in a similar manner to the known compounds. The compounds of formula VIII are known compounds or can be prepared in accordance with known procedures.

The compounds of formula I and their tautomers possess antiviral activity and can be used in the control or prevention of viral infections, for example of herpes simplex viral infections. The in vitro activity of these compounds in inhibiting herpes simplex virus type 2 (HSV-2) thymidine kinase can be demonstrated by means of the following test procedure:

The assay mixture contains 50 mM Tris-HCl, pH 8, 5 mM magnesium chloride, 5 mM ATP, 0.3 μM $^3$H-thymidine (50 Ci/mmol), suitably diluted thymidine kinase extract and various concentrations of the test compounds in a total volume of 100 μl. Assays are incubated at 37° C. for 30 minutes and the reaction is terminated by immersion in a boiling water bath for 2 minutes. 85 μl aliquots from each assay are then dried on cellulose paper discs and the unphosphorylated $^3$H-thymidine is removed by washing in 4 mM ammonium formate. The radioactivity remaining bound to the discs is then measured by scintillation spectrophotometry. The degree of inhibition at each concentration of the test compound is expressed as a percentage of a control reaction. The IC$_{50}$ value, namely the concentration of the test compound which inhibits enzyme activity by 50%, is then calculated. The results obtained with representative compounds of formula I are compiled in the following Table:

TABLE

| Compound of Example No. | IC$_{50}$ (μM) |
| --- | --- |
| 3 | 0.0024 |
| 5 | 0.016 |
| 7 | 0.17 |
| 9 | 0.6 |
| 14c | 0.072 |

The compounds of formula I and their tautomers can be used as medicaments in the form of pharmaceutical preparations which contain them in association with a compatible pharmaceutical carrier material. This can be an organic or inorganic carrier suitable for enteral, e.g. oral, or parenteral administration. Examples of such carriers are water, gelatin, gum arabic, lactose, starch, magnesium stearate, talc, vegetable oils, polyalkylene glycols and petroleum jelly. The pharmaceutical preparations can be made up in a solid form, e.g. as tablets, dragees, suppositories or capsules, or in a liquid form, e.g. as solutions, suspensions or emulsions; they may be subjected to standard pharmaceutical operations, e.g. sterilization and/or may contain adjuvants, e.g. preserving, stabilizing, wetting or emulsifying agents, salts for varying the osmotic pressure or buffers. They may also contain other therapeutically valuable substances.

The compounds of formula I and their tautomers can be administered to warm-blooded animals in need thereof for the control or prevention of viral infections, for example of herpes simplex viral infections.

The compounds of formula I and their tautomers can be administered to adult humans in a daily dosage of from about 1 to 1000 mg, preferably about 5 to 500 mg. The daily dosage may be administered as a single dose or in divided doses. The above dosage range is given by way of example only and can be varied upwards or downwards depending on factors such as the particular compound being administered, the route of administration, the severity of the indication being treated and the condition of the patient.

EXAMPLE 1

A solution of 3.30 g of (E)-3'-O-acetyl-5'-[3-(2,6-dichlorophenyl)-2-oxopropylidene]-2',5'-dideoxy-5-ethyluridine in 1.50 l of methanol was hydrogenated over 1.10 g of 10% Pd/C catalyst at room temperature and under atmospheric pressure for 3 hours. The mixture was filtered and the filtrate was evaporated. The residue was triturated with diethyl ether to give 2.45 g of 3'-O-acetyl-5'-[3-(2,6-dichlorophenyl)-2-oxopropyl]-2',5'-dideoxy-5-ethyluridine, mp 186°.

The starting material was prepared as follows:

(A) 50 ml of oxalyl chloride and 0.5 ml of dimethylformamide were added to a stirred suspension of 5.12 g of (2,6-dichlorophenyl)acetic acid in 120 ml of toluene. The mixture was stirred at room temperature for 2.5 hours and then evaporated to dryness. The residue was suspended in 40 ml of diethyl ether and the suspension was added gradually to 250 ml of a 0.25M solution of diazomethane in diethyl ether. The mixture was stirred at room temperature for 2 hours and then cooled to 0° C. Hydrogen chloride was then bubbled through the mixture for 10 minutes. 300 ml of water were added to the mixture and the phases were separated. The organic phase was washed with 200 ml of saturated sodium hydrogen carbonate solution and 300 ml of water, dried over anhydrous sodium sulphate and evaporated to give 6.04 g of 1-chloro-3-(2,6-dichlorophenyl)-2-propanone in form of a white solid. This solid was taken up in 21 ml of chloroform, 7.19 g of triphenylphosphine were added and the solution was stirred and heated under reflux for 6 hours. The mixture was cooled and poured into 200 ml of diethyl ether. The resulting precipitate was collected, washed with diethyl ether and dried to give 8.605 g of [3-(2,6-dichlorophenyl)-2-oxopropyl]triphenylphosphonium chloride in the form of a white solid. This solid was taken up in 1.5 l of warm water and the mixture was filtered. The filtrate was stirred while 12.5 ml of 5% sodium hydroxide solution were added. The mixture was extracted twice with 600 ml of diethyl ether each time and the combined extracts were washed with 1 l of water, dried over anhydrous sodium sulphate and evaporated. The residue was recrystallized from 150 ml of diethyl ether and yielded 4.286 g of [3-(2,6-dichlorophenyl)-2-oxopropylidene]triphenylphorphorane of melting point 98°-100° C.

(B) A solution of 2.759 g of 3'-O-acetyl-2'-deoxy-5-ethyluridine, 5.75 g of dicyclohexylcarbodiimide and 0.375 ml of dichloroacetic acid in 24 ml of dimethyl sulphoxide was stirred at room temperature for 27 hours. 0.375 ml of pyridine and 4.286 g of [3-(2,6-dichlorophenyl)-2-oxopropylidene]triphenylphosphorane were added and the mixture was stirred for a further 23 hours. The mixture was filtered and the filtrate was evaporated. The residue was dissolved in 100 ml of ethyl acetate and the solution was washed twice with 100 ml of water each time, dried over anhydrous sodium sulphate and evaporated. The resulting gum was subjected to flash chromatography on a column of silica gel using ethyl acetate/hexane (2:1) for the elution. There were obtained 3.84 g of (E)-3'-O-acetyl-5'-[3-(2,6-dichlorophenyl)-2-oxopropylidene]-2',5'-dideoxy-5-ethyluridine in form of a white solid of melting point 165° C.

EXAMPLE 2

Analogously to Example 1, there were obtained:

(a) from (E)-3'-O-acetyl-2',5'-dideoxy-5-ethyl-5'-[3-(2,6-dimethylphenyl)-2-oxopropylidene]uridine, mp 126°-130° C., which was prepared in a manner analogous to that described in Example 1(A) and (B) starting from (2,6-dimethylphenyl)acetic acid:

3'-O-acetyl-2',5'-dideoxy-5-ethyl-5'-[3-(2,6-dimethylphenyl)-2-oxopropyl]uridine, mp 150°-150.5° C.

Similarly, in a manner analogous to that described in Example 1(A) and (B), in (b) through (e) just below:

(b) from (E)-3'-O-acetyl-2',5'-dideoxy-5-ethyl-5'-[3-(2-methylphenyl)-2-oxopropylidene]uridine, mp 124°-126° C., which was prepared from (2-methylphenyl)acetic acid:

3'-O-acetyl-2',5'-dideoxy-5-ethyl-5'-[3-(2-methylphenyl)-2-oxopropyl]uridine, mp 156.5° C.

(c) from (E)-3'-O-acetyl-5'-[3-(2-chlorophenyl)-2-oxopropylidene]-2',5'-dideoxy-5-ethyluridine, mp 144°-145° C., which was prepared from (2-chlorophenyl)acetic acid:

3'-O-acetyl-5'-[3-(2-chlorophenyl)-2-oxopropyl]-2',5'-dideoxy-5-ethyluridine, mp 168.5° C.

(d) from (E)-3'-O-acetyl-2',5'-dideoxy-5-ethyl-5'-(2-oxo-3-phenylpropylidene)uridine, which was prepared from phenylacetic acid:

3'-O-acetyl-2',5'-dideoxy-5-ethyl-5'-(2-oxo-3-phenylpropyl)uridine, nmr (CDCl$_3$); δ1.10 (t, 3), 1.85-2.03 (m, 2), 2.10 (s, 3), 2.10-2.18 (m, 1), 2.30-2.40 (m, 3), 2.57-2.75 (m, 2), 3.72 (s, 2), 3.93 (m, 1), 4.97 (m, 1), 6.27 (dd, 1), 7.03 (s, 1), 7.17-7.35 (m, 5), 8.83 (s, 1)

(e) from (E)-3'-O-acetyl-2',5'-dideoxy-5-ethyl-5'-(2-oxo-3-phenylbutylidene)uridine, which was prepared from 2-phenylpropanoic acid:

3'-O-acetyl-2',5'-dideoxy-5-ethyl-5'-[2-oxo-3(RS)-phenylbutyl]uridine, nmr (CDCl$_3$); δ1.07-1.17 (dt, 3), 1.35-1.42 (dd, 3), 1.72-2.02 (m, 2), 2.05-2.13 (m, 1), 2.07 (s, 3), 2.30-2.43 (m, 3), 2.50-2.60 (m, 2), 3.72-3.82 (m, 1), 3.89 (m, 1), 4.94 (m, 1), 6.20 (m, 1), 7.01 (d, 1), 7.19-7.35 (m, 5), 8.52 (d, 1).

EXAMPLE 3

A solution of 2 g of 3'-O-acetyl-5'-[3-(2,6-dichlorophenyl)-2-oxopropyl]-2',5'-dideoxy-5-ethyluridine in 45 ml of 0.1M methanolic sodium methoxide solution was stirred at room temperature for 1.5 hours. The solution was diluted with 500 ml of methanol, a polystyrene divinyl benzene cation exchange resin containing sulphonic acid groups (H$^+$ form) was added, the mixture was stirred for 10 minutes and then filtered. The filtrate was evaporated and the residue was triturated with diethyl ether to give 1.72 g of 5'-[3-(2,6-dichlorophenyl)-2-oxopropyl]-2',5'-dideoxy-5-ethyluridine, mp 229°-230° C.

EXAMPLE 4

Analogously to Example 3, there were obtained:

(a) from 3'-O-acetyl-2',5'-dideoxy-5-ethyl-5'-(2-oxo-3-phenylpropyl)uridine:

2',5'-dideoxy-5-ethyl-5'-(2-oxo-3-phenylpropyl)uridine, mp 148°-151° C.

(b) from 3'-O-acetyl-2',5'-dideoxy-5-ethyl-5'-[3-(2-methylphenyl)-2-oxopropyl]uridine:

2',5'-dideoxy-5-ethyl-5'-[3-(2-methylphenyl)-2-oxopropyl]uridine, mp 165° C.

(c) from 3'-O-acetyl-2',5'-dideoxy-5-ethyl-5'-[3-(2,6-dimethylphenyl)-2-oxopropyl]uridine:

2',5'-dideoxy-5-ethyl-5'-[3-(2,6-dimethylphenyl)-2-oxopropyl]uridine, mp 223°-224° C.

(d) from 3'-O-acetyl-5'-[3-(2-chlorophenyl)-2-oxopropyl]-2',5'-dideoxy-5-ethyluridine:

5'-[3-(2-chlorophenyl)-2-oxopropyl]-2',5'-dideoxy-5-ethyluridine, mp 180°-181° C.

(e) from 3'-O-acetyl-2',5'-dideoxy-5-ethyl-5'-[2-oxo-3(RS)-phenylbutyl]uridine:

2',5'-dideoxy-5-ethyl-5'-[2-oxo-3(RS)-phenylbutyl]uridine, mp 145° C.

EXAMPLE 5

A solution of 149 mg of 3'-O-acetyl-5'-[3-(2,6-dichlorophenyl)-2-oxopropyl]-2',5'-dideoxy-5-ethyluridine and 26 mg of sodium borohydride in 7 ml of dimethoxyethane was stirred at room temperature for 2.5 hours. The solvent was removed by evaporation and the residue was taken up in 22 ml of 5% ammonium chloride solution and extracted twice with 20 ml of ethyl acetate each time. The extracts were washed with 20 ml of water, dried over anhydrous sodium sulphate and evaporated to give 3'-O-acetyl-5'-[3-(2,6-dichlorophenyl)-2(RS)-hydroxypropyl]-2',5'-dideoxy-5-ethyluridine in the form of a colourless gum. This was dissolved in 3 ml of 0.1M sodium methoxide solution and stirred at room temperature for 1 hour. The solution was then diluted with 150 ml of methanol, stirred with a cross-linked polystyrene/divinyl benzene cation exchange resin containing sulphonic acid groups (H$^+$ form) and then filtered. The filtrate was evaporated and the residue was crystallized from ethanol to give 45 mg of 5'-[3-(2,6-dichlorophenyl)-2(RS)-hydroxypropyl]-2',5'-dideoxy-5-ethyluridine, mp 185°-186° C.

EXAMPLE 6

Analogously to Example 5, there were obtained:

(a) from 3'-O-acetyl-2',5'-dideoxy-5-ethyl-5'-(3-phenyl-2-oxopropyl)uridine:

2',5'-dideoxy-5-ethyl-5'-[2(RS)-hydroxy-3-phenylpropyl]uridine, mp 142° C.

(b) from 3'-O-acetyl-2',5'-dideoxy-5-ethyl-5'-[3-(2-methylphenyl)-2-oxopropyl]uridine:

2',5'-dideoxy-5-ethyl-5'-[2(RS)-hydroxy-3-(2-methylphenyl)propyl]uridine, mp 161.5°-163° C.

(c) from 3'-O-acetyl-5'-[3-(2-chlorophenyl)-2-oxopropyl]-2',5'-dideoxy-5-ethyluridine:

5'-[3-(2-chlorophenyl-2(RS)-hydroxypropyl]-2',5'-dideoxy-5-ethyluridine, mp 215°-217° C.

(d) from 3'-O-acetyl-2',5'-dideoxy-5-ethyl-5'-[3-(2,6-dimethylphenyl)-2-oxopropyl]uridine:

2',5'-dideoxy-5-ethyl-5'-[2(RS)-hydroxy-3-(2,6-dimethylphenyl)propyl]uridine, mp 174°-178° C.

EXAMPLE 7

A solution of 300 mg of 3'-O-acetyl-5'-[2(RS)-hydroxy-3-phenylpropyl]-2',5'-dideoxy-5-ethyluridine and 0.2 ml of methanesulphonyl chloride in 5 ml of pyridine was left to stand at 0° C. overnight. The mixture was poured on to 40 ml of ice/water, stirred and extracted with 40 ml of ethyl acetate. The extract was dried over anhydrous sodium sulphate and evaporated to yield 330 mg of 3'-O-acetyl-2',5'-dideoxy-5-ethyl-5'-[2(RS)-methanesulphonyloxy-3-phenylpropyl]uridine.

A mixture of 240 mg of the latter and 190 mg of sodium iodide in 5 ml of acetone was stirred and heated under reflux for 5.5 hours. The mixture was allowed to cool and was then filtered. The filtrate was evaporated. The residue was taken up in 50 ml of dichloromethane and washed with 50 ml of water, twice with 50 ml of 5% sodium thiosulphate solution each time and 50 ml of water, dried over anhydrous sodium sulphate and evaporated to yield 250 mg of 3'-O-acetyl-2',5'-dideoxy-5-ethyl-5'-[2(RS)-iodo-3-phenylpropyl]uridine.

A solution of 80 mg of the latter in 5 ml of ethanol was saturated with ammonia. 50 mg of palladium on barium sulphate catalyst were added and the mixture was hydrogenated at room temperature and under atmospheric pressure for 3 days. The mixture was filtered and the filtrate was evaporated. The residue was extracted with several portions of ethyl acetate and the combined extracts were evaporated to give 70 mg of 3'-O-acetyl-2',5'-dideoxy-5-ethyl-5'-(3-phenylpropyl)uridine.

A solution of 70 mg of the latter in 2 ml of 0.1M sodium methoxide solution was stirred at room temperature for 1 hour. A polystyrene divinyl benzene cation exchange resin containing sulphonic acid groups (H+ form) was added and the mixture was stirred and filtered. The filtrate was evaporated and the residue was triturated with diethyl ether to give 22 mg of 2',5'-dideoxy-5-ethyl-5'-(3-phenylpropyl)uridine, mp 160°–162° C.

EXAMPLE 8

A solution of 0.5 g of benzyl mercaptan in 10 ml of dry dimethylformamide was treated with 60 mg of a 80% dispersion of sodium hydride in mineral oil. After the effervescence had ceased a solution of 1.64 g of 2'-deoxy-5-ethyl-5'-O-(p-toluenesulphonyl)uridine in 20 ml of dry dimethylformamide was added. The mixture was stirred and heated at 100° C. under a nitrogen gas atmosphere. The course of the reaction was followed by thin layer chromatography. After 4 hours the mixture was evaporated to give an oily residue. This was purified by flash column chromatography on silica gel using methanol/dichloromethane (1:9) for the elution. The fractions containing the product were combined and evaporated to yield an oil which solidified and was recrystallized from diethyl ether to give 1.46 g of 5'-benzylthio-2',5'-dideoxy-5-ethyluridine, mp 149°–151° C.

EXAMPLE 9

1 g of 5'-benzylthio-2',5'-dideoxy-5-ethyluridine was dissolved in 10 ml of glacial acetic acid and the solution was cooled to 0° C., whereupon 0.9 ml of 30% hydrogen peroxide was added. The mixture was stirred at 0° C. for 1 hour and then at room temperature for 17 hours. The acetic acid was removed by evaporation and the resulting solid was crystallized from approximately 100 ml of methanol to give 0.43 g of 5'-benzylsulphonyl-2',5'-dideoxy-5-ethyluridine of melting point 232°–233° C.

EXAMPLE 10

In a manner analogous to that described in Example 1, from (E)-3'-O-acetyl-5'-[3(RS)-(2,4-dichlorophenoxy)-2-oxobutylidene]-2',5'-dideoxy-5-ethyluridine, prepared in a manner analogous to that described in Example 1(A) and (B) starting from 2(RS)-(2,4-dichlorophenoxy)propionic acid, there was obtained:
3'-O-acetyl-5'-[3(RS)-(2,4-dichlorophenoxy)-2-oxobutyl]2',5'-dideoxy-5-ethyluridine of melting point 122°–142° C.

EXAMPLE 11

In a manner analogous to that described in Example 3, from 3'-O-acetyl-5'-[3(RS)-(2,4-dichlorophenoxy)-2-oxobutyl]-2',5'-dideoxy-5-ethyluridine there was obtained 5'-[3(RS)-(2,4-dichlorophenoxy)-2-oxobutyl]-2',5'-dideoxy-5-ethyluridine, mp 157°–159° C.

EXAMPLE 12

In a manner analogous to that described in Example 5, from 3'-O-acetyl-5'-[3(RS)-(2,4-dichlorophenoxy)-2-oxobutyl]-2',5'-dideoxy-5-ethyluridine there was obtained 5'-[3(RS)-(2,4-dichlorophenoxy)-2(RS)-hydroxybutyl]-2',5'-dideoxy-5-ethyluridine of melting point 108°–111° C.

EXAMPLE 13

In a manner analogous to that described in Example 7, from 3',-O-acetyl-2',5'-dideoxy-5-ethyl-5'-[2(RS)-hydroxy-3-(2,6-dimethylphenyl)propyl]uridine there was obtained 2',5'-dideoxy-5-ethyl-5'-[3-(2,6-dimethylphenyl)propyl]uridine of melting point 213.5°–214° C.

EXAMPLE 14

Analogously to Example 8, there was obtained:
(a) from 2'-deoxy-5-ethyl-5'-O-(p-toluenesulphonyl)uridine and 2-chlorobenzyl mercaptan:
5'-(2-chlorobenzylthio)-2',5'-dideoxy-5-ethyluridine, mp 147°–148° C.

(b) from 2'-deoxy-5-ethyl-5'-O-(p-toluenesulphonyl)uridine and 2,4-dichlorobenzyl mercaptan:
5'-(2,4-dichlorobenzylthio)-2',5'-dideoxy-5-ethyluridine, mp 169°–170° C.

(c) from 2'-deoxy-5-ethyl-5'-O-(p-toluenesulphonyl)uridine and 2,6-dichlorobenzyl mercaptan:
5'-(2,6-dichlorobenzylthio)-2',5'-dideoxy-5-ethyluridine, mp 206°–207° C.

EXAMPLE 15

Analogously to Example 9, there was obtained:
(a) from 5'-(2-chlorobenzylthio)-2',5'-dideoxy-5-ethyluridine:
5'-(2-chlorobenzylsulphonyl)-2',5'-dideoxy-5-ethyluridine, mp 189°–190° C.

(b) from 5'-(2,4-dichlorobenzylthio)-2',5'-dideoxy-5-ethyluridine:
5'-(2,4-dichlorobenzylsulphonyl)-2',5'-dideoxy-5-ethyluridine, mp 217°–218° C.

(c) from 5'-(2,6-dichlorobenzylthio)-2',5'-dideoxy-5-ethyluridine:
5'-(2,6-dichlorobenzylsulphonyl)-2',5'-dideoxy-5-ethyluridine, mp 236°–237° C.

The following Example illustrates a pharmaceutical preparation containing the compounds of formula I:

Tablets containing the following ingredients may be prepared in a conventional manner:

| Ingredient | Per tablet |
| --- | --- |
| Compound of formula I | 100 mg |
| Lactose | 70 mg |
| Maize stacrh | 70 mg |
| Polyvinylpyrrolidone | 5 mg |
| Magnesium stearate | 5 mg |
| Tablet weight | 250 mg |

What is claimed is:
1. A compound of the formula

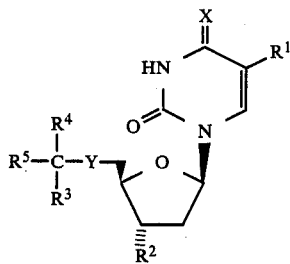

wherein $R^1$ is halogen, $C_{1-4}$-alkyl or halo-($C_{1-4}$-alkyl), $R^2$ is hydrogen, hydroxy or cyclopentylpropionyloxy, phenylacetoxy, benzoyloxy or $C_{1-4}$-alkanoyloxy $R^3$ and $R^4$ each are hydrogen or $C_{1-4}$-alkyl, $R^5$ is unsubstituted phenyl or phenyl carrying one or more substituents selected from the group consisting of halogen, hydroxy, $C_{1-4}$-alkyl, $C_{1-4}$-alkoxy, trifluoromethyl, nitro and phenyl; or unsubstituted phenyloxy or phenyloxy carrying one or more substituents selected from the group consisting of halogen, hydroxy, $C_{1-4}$-alkyl, $C_{1-4}$-alkoxy, trifluoromethyl, nitro, and phenyl, X is O or NH and Y is —CO—CH$_2$—, —CH(OH)—CH$_2$—, —CH$_2$—CH$_2$—, —SO— or —SO$_2$—, or a tautomer thereof.

2. A compound according to claim 1 wherein $R^1$ is $C_{1-4}$-alkyl.

3. A compound according to claim 1 wherein $R^2$ is hydroxy or $C_{1-4}$-alkanoyloxy.

4. A compound according to claim 1 wherein $R^3$ and $R^4$ each are hydrogen.

5. A compound according to claim 1 wherein $R^5$ is dihalophenyl.

6. A compound according to claim 1 wherein X is O.

7. A compound according to claim 1 wherein Y is —CO—CH$_2$—, —CH(OH)—CH$_2$—, —CH$_2$—CH$_2$— or —SO$_2$—.

8. A compound according to claim 1 wherein $R^1$ is ethyl, $R^2$ is hydroxy or acetoxy, $R^3$ and $R^4$ each are hydrogen, $R^5$ is 2,6-dichlorophenyl, X is O and Y is —CO—CH$_2$— or —CH(OH)—CH$_2$.

9. A compound according to claim 1, selected from the group consisting of
3'-O-Acetyl-5'[3-(2,6-dichlorophenyl)-2-oxopropyl]-2',5'-dideoxy-5-ethyluridine,
5'-[3-(2,6-dichlorophenyl)-2(RS)-hydroxypropyl]-2',5'-dideoxy-5-ethyluridine and
5'-[3-(2,6-dichlorophenyl)-2-oxopropyl]-2',5'-dideoxy-5-ethyluridine.

10. A compound according to claim 1, selected from the group consisting of
3'-O-Acetyl-2',5'-dideoxy-5-ethyl-5'-[3-(2,6-dimethylphenyl)-2-oxopropyl]uridine,
3'-O-acetyl-2',5'-dideoxy-5-ethyl-5'-[3-(2-methylphenyl)-2-oxopropyl]uridine,
3'-O-acetyl-5'-[3-(2-chlorophenyl)-2-oxopropyl]-2',5'-dideoxy-5-ethyluridine,
3'-O-acetyl-2',5'-dideoxy-5-ethyl-5'-(2-oxo-3-phenylpropyl)uridine,
3'-O-acetyl-2',5'-dideoxy-5-ethyl-5'-[2-oxo-3(RS)-phenylbutyl]uridine,
2',5'-dideoxy-5-ethyl-5'-(2-oxo-3-phenylpropyl)uridine,
2',5'-dideoxy-5-ethyl-5'-[3-(2-methylphenyl)-2-oxopropyl]uridine,
2',5'-dideoxy-5-ethyl-5'-[3-(2,6-dimethylphenyl)-2-oxopropyl]uridine,
5'-[3-(2-chlorophenyl)-2-oxopropyl]-2',5'-dideoxy-5-ethyluridine,
2',5'-dideoxy-5-ethyl-5'-[2-oxo-3(RS)-phenylbutyl]uridine,
2',5'-dideoxy-5-ethyl-5'-[2(RS)-hydroxy-3-phenylpropyl]uridine,
2',5'-dideoxy-5-ethyl-5'-[2(RS)-hydroxy-3-(2-methylphenyl)propyl]uridine,
5'-[3-(2-chlorophenyl)-2(RS)-hydroxypropyl]-2',5'-dideoxy-5-ethyluridine,
2',5'-dideoxy-5-ethyl-5'-[2(RS)-hydroxy-3-(2,6-dimethylphenyl)propyl]uridine,
2',5'-dideoxy-5-ethyl-5'-(3-phenylpropyl)uridine and
5'-benzylsulphonyl-2',5'-dideoxy-5-ethyluridine.

11. A compound according to claim 1, selected from the group consisting of
2',5'-Dideoxy-5'-[3-(2,6-dimethylphenyl)-2-oxopropyl]uridine,
3'-O-acetyl-5'-[3(RS)-(2,4-dichlorophenoxy)-2-oxobutyl]-2',5'-dideoxy-5-ethyluridine,
5'-[3(RS)-(2,4-dichlorophenoxy)-2-oxobutyl]-2',5'-dideoxy-5-ethyluridine,
5'-[3(RS)-(2,4-dichlorophenoxy)-2(RS)-hydroxybutyl]-2',5'-dideoxy-5-ethyluridine,
5'-(2-chlorobenzylsulphonyl)-2',5'-dideoxy-5-ethyluridine,
5'-(2,4-dichlorobenzylsulphonyl)-2',5'-dideoxy-5-ethyluridine and
5'-(2,6-dichlorobenzylsulphonyl)-2',5'-dideoxy-5-ethyluridine.

12. A composition comprising an amount effective for inhibiting herpes simplex virus type 2 (HSV-2) thymidine kinase in vitro of a compound of the formula

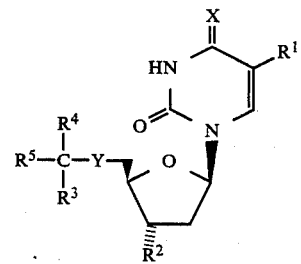

wherein $R^1$ is halogen, $C_{1-4}$-alkyl or halo-($C_{1-4}$-alkyl), $R^2$ is hydrogen, hydroxy or cyclopentylpropionyloxy, phenylacetoxy, benzoyloxy or $C_{1-4}$-alkanoyloxy $R^3$ and $R^4$ each are hydrogen or $C_{1-4}$-alkyl, $R^5$ is unsubstituted phenyl or phenyl carrying one or more substituents selected from the group consisting of halogen, hydroxy, $C_{1-4}$-alkyl, $C_{1-4}$-alkoxy, trifluoromethyl, nitro and phenyl; or unsubstituted phenyloxy or phenyloxy carrying one or more substituents selected from the group consisting of halogen, hydroxy, $C_{1-4}$-alkyl, $C_{1-4}$-alkoxy, trifluoromethyl, nitro, and phenyl, X is O or NH and Y is —CO—CH$_2$—, —CH(OH)—CH$_2$—, —CH$_2$—CH$_2$—, —SO— or —SO$_2$—, or a tautomer thereof, and a pharmaceutical carrier material.

13. A composition in accordance with claim 12, wherein the compound of formula I is 5'-[3-(2,6-dichlorophenyl)-2-oxopropyl]-2',5'-dideoxy-5-ethyluridine.

14. A method for inhibiting herpes simplex virus type 2 (HSV-2) thymidine kinase which comprises administering an amount effective for inhibiting herpes simplex virus type 2 (HSV-2) thymidine kinase in vitro of a compound of the formula

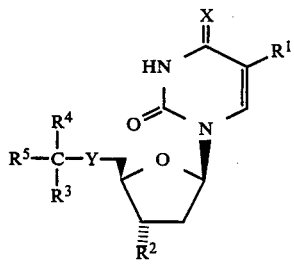

I wherein $R^1$ is halogen, $C_{1-4}$-alkyl or halo-($C_{1-4}$-alkyl), $R^2$ is hydrogen, hydroxy or cyclopentylpropionyloxy, phenylacetoxy, benzoyloxy or $C_{1-4}$-alkanoyloxy $R^3$ and $R^4$ each are hydrogen or $C_{1-4}$-alkyl, $R^5$ is unsubstituted phenyl or phenyl carrying one or more substituents selected from the group consisting of halogen, hydroxy, $C_{1-4}$-alkyl, $C_{1-4}$-alkoxy, trifluoromethyl, nitro and phenyl; or unsubstituted phenyloxy or phenyloxy carrying one or more substituents selected from the group consisting of halogen, hydroxy, $C_{1-4}$-alkyl, $C_{1-4}$-alkoxy, trifluoromethyl, nitro, and phenyl, X is O or NH and Y is —CO—CH$_2$—, —CH(OH)—CH$_2$—, —CH$_2$—CH$_2$—, —SO— or —SO$_2$—, or a tautomer thereof.

15. A method in accordance with claim 14, wherein the compound of formula I is 5'-[3-(2,6-dichlorophenyl)-2-oxopropyl]-2',5'-dideoxy-5-ethyluridine.

* * * * *